United States Patent
Koike et al.

(10) Patent No.: US 7,901,559 B2
(45) Date of Patent: Mar. 8, 2011

(54) POLYACRYLAMIDE GEL FOR ELECTROPHORESIS, POLYACRYLAMIDE GEL ELECTROPHORESIS METHOD USING THE SAME, METHOD OF PRODUCING THE SAME, AND ACRYLAMIDE COMPOUND

(75) Inventors: Tohru Koike, Hiroshima (JP); Akihiko Kawasaki, Amagasaki (JP); Tatsuhiro Kobashi, Amagasaki (JP)

(73) Assignee: Nard Institute, Ltd. (JP)

( * ) Notice: Subject to any disclaimer, the term of this patent is extended or adjusted under 35 U.S.C. 154(b) by 555 days.

(21) Appl. No.: 11/988,968

(22) PCT Filed: Aug. 1, 2005

(86) PCT No.: PCT/JP2005/014469
§ 371 (c)(1),
(2), (4) Date: Jan. 17, 2008

(87) PCT Pub. No.: WO2007/015312
PCT Pub. Date: Feb. 8, 2007

(65) Prior Publication Data
US 2010/0108515 A1    May 6, 2010

(51) Int. Cl.
*G01N 27/26* (2006.01)
*C07D 213/56* (2006.01)
*C07D 213/64* (2006.01)
*C07D 213/65* (2006.01)
*C07D 213/68* (2006.01)
*C07D 213/72* (2006.01)
*C07D 213/78* (2006.01)
*C07D 471/22* (2006.01)

(52) U.S. Cl. ......... 204/456; 204/469; 204/606; 546/261; 546/262; 546/263; 546/264; 546/265; 546/267; 546/27; 524/555; 526/303.1

(58) Field of Classification Search ......... 204/451–470, 204/606; 546/27, 255, 285, 261–265, 267; 524/555; 526/303.1
See application file for complete search history.

(56) References Cited

U.S. PATENT DOCUMENTS

| | | | |
|---|---|---|---|
| 5,237,016 A * | 8/1993 | Ghosh et al. | 525/329.4 |
| 5,264,101 A | 11/1993 | Demorest et al. | |
| 5,567,292 A | 10/1996 | Madabhushi et al. | |
| 6,926,815 B2 | 8/2005 | Liu et al. | |
| 7,195,925 B2 | 3/2007 | Ohnishi et al. | |
| 7,358,363 B2 * | 4/2008 | Koike et al. | 546/27 |
| 2005/0038258 A1 | 2/2005 | Koike et al. | |

FOREIGN PATENT DOCUMENTS

| | | |
|---|---|---|
| JP | 2004-294425 | 10/2004 |
| JP | 2004-305024 | 11/2004 |
| JP | 2005-351765 | 12/2005 |
| WO | WO 93/22665 | 11/1993 |
| WO | WO 95/16911 | 6/1995 |
| WO | WO 00/42423 | 7/2000 |
| WO | WO 02/16454 | 2/2002 |
| WO | WO 03/053932 | * 7/2003 |

OTHER PUBLICATIONS

Eiji Konoshita et al.—"Phosphase-binding Tag, a New Tool to Visualize Phosphorylated Proteins"—Molecular & Cellular Proteomics, vol. 5, No. 4, Dec. 11, 2005.

* cited by examiner

*Primary Examiner* — Alexa D Neckel
*Assistant Examiner* — Jennifer Dieterle
(74) *Attorney, Agent, or Firm* — Gerald E. Hespos; Michael J. Porco

(57) ABSTRACT

It is intended to provide a method for easily detecting a phosphorylated peptide (protein) in a test sample by using SDS-polyacrylamide gel electrophoresis (SDS-PAGE) which has been conventionally employed in analyzing a protein; a polyacrylamide gel for electrophoresis to be used in the method; a method of producing the gel; and a synthesizing intermediate in producing the gel. The polyacrylamide gel for electrophoresis to be used in the method of the invention is characterized in that at least a part of the structure thereof has a structure represented by the following formula (I); wherein $M^{2+}$ represents a transition metal ion; and X represents a linker group.

(I)

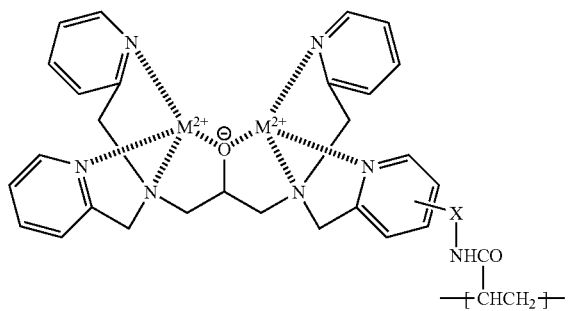

6 Claims, 2 Drawing Sheets

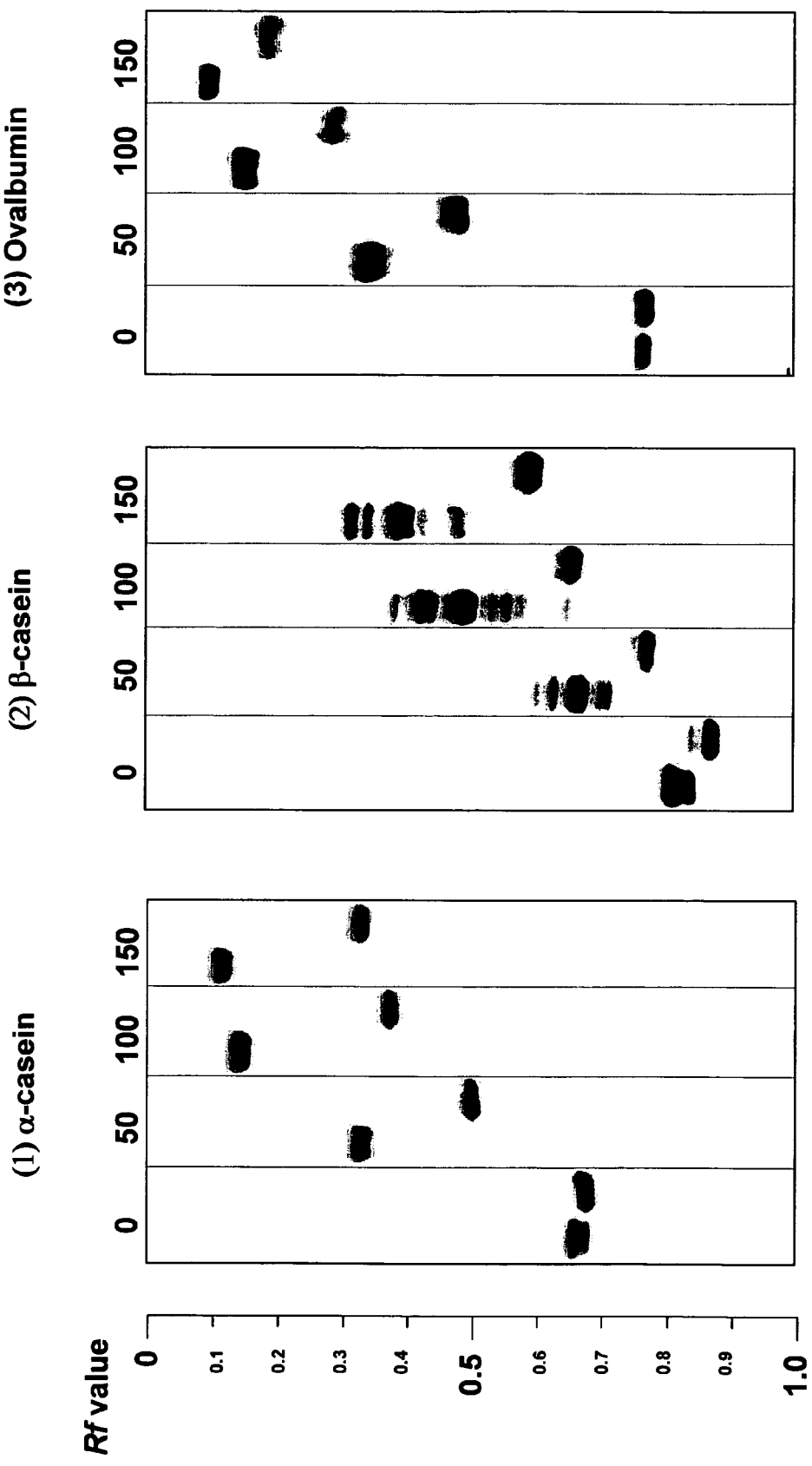

POLYACRYLAMIDE GEL FOR ELECTROPHORESIS, POLYACRYLAMIDE GEL ELECTROPHORESIS METHOD USING THE SAME, METHOD OF PRODUCING THE SAME, AND ACRYLAMIDE COMPOUND

BACKGROUND OF THE INVENTION

1. Field of the Invention

The present invention relates to a polyacrylamide gel for electrophoresis, a polyacrylamide gel electrophoresis method using the gel, a method of producing the gel, and an acrylamide compound.

2. Description of the Related Art

Some kinds of biological enzymes have serine, threonine, and tyrosine residuals at a specific site such as an active center or an allosteric site and an enzyme activity is regulated by phosphorylation or dephosphorylation of their hydroxyl groups by an enzyme called as kinase. Further, there are enzymes whose activity is regulated by phosphorylation or dephosphorylation of amino or imino groups of lysine, arginine and histidine, or carboxyl groups of aspartic acid and glutamic acid.

As a metabolism system regulated by such phosphorylation-dephosphorylation, a glycogen synthesis and decomposition system is well known. This metabolism system is cascade-controlled and regulated mainly by phosphorylation-dephosphorylation.

Recently, it has been made clear that this phosphorylation-dephosphorylation plays an important role in a metabolism system relevant to disease. For example, it is considered that the abnormality of the phosphorylation-dephosphorylation is one of causes of cell canceration. That is, advancement and cease of cell cycles are controlled by phosphorylation or dephosphorylation of various enzymes (proteins), and cyclin and cyclin-dependent kinase (CDK) are relevant to the phosphorylation or dephosphorylation, but if such a mechanism is damaged, phosphorylation (dephosphorylation) is disordered and accordingly, abnormal propagation of cells is to be induced.

In addition, the following have been made clear: proteinkinase C is relevant to degranulation of mast cells to be a cause of allergy disease such as atopic dermatitis and hay fever; neurofibrillary change occurred in the brain of a patient suffering from Alzheimer disease is due to phosphorylated tau protein.

Accordingly, understanding of the phosphorylation-dephosphorylation state of protein may possibly be useful for not only search of gene expression of cells in body tissues and enzyme activity evaluation but also diagnosis and treatment of disease.

However, methods of specifying phosphorylated protein or dephosphorylated protein employed conventionally have various disadvantages. For example, an enzyme immunization method has an advantage that analysis is possible even if the amount of a protein sample as a target is slight. However, it is difficult to sufficiently obtain a needed antibody and in the case where the target protein is in several kDa or less, it is impossible to prepare an antibody to be bonded at the phosphorylation site of the protein.

A method for detecting specific bonding to protein by using phosphoric acid labeled with a radioactive isotope $^{32}P$ is supposed to be possible. However, carefulness is certainly required in handling the radioactive isotope and it is also necessary to dispose and treat a waste solution.

Further, it is supposed to be possible to apply a two-dimensional electrophoresis method since phosphorylated protein and dephosphorylated protein have different electric charges separately. However, since there are no less than 5 kinds of amino acids such as aspartic acid and lysine having electric charge in the side chains among 20 kinds of amino acids composing protein, it is assumed that the electric charge alteration by the phosphorylation or dephosphorylation is small relative to the electric charge of the protein itself. In such a case, it is difficult for the electrophoresis method depending on the electric charge to detect phosphorylation or dephosphorylation. Particularly, in the case of analyzing a biological sample, since many types of proteins are contained in the sample, the detection is impossible only on the basis of slight band position change. In addition, if a radioactive isotope is employed for spot specification, the above-mentioned problem occurs.

WO03/053932 discloses a compound having specific and high coordination ability for a phosphate group, and a method of specifying phosphorylated peptide by adding the compound to a sample and then changing the charge of the phosphated peptide to carry out electrophoresis. However, there is no description of a compound having a side chain including an acrylamide structure, and a more sensitive phosphorylated peptide detection method is required.

SUMMARY OF THE INVENTION

Under the above-mentioned situation, to solve the problems, the invention provides a method for easily detecting a phosphate peptide (protein) in a test sample by using SDS-polyacrylamide gel electrophoresis (SDS-PAGE) which has been conventionally employed in analyzing a protein; a polyacrylamide gel for electrophoresis to be used in the above method; a method of producing the gel; and a synthesizing intermediate in producing the gel.

To solve the above-mentioned problems, the inventors of the invention have made various investigations on a method for separating and identifying a phosphorylated peptide from other peptides in SDS-PAGE. Accordingly, the inventors have found that a phosphorylated peptide can be specifically detected even from a test sample containing a large number of peptides if a compound of the invention having a structure having an extremely high coordination linkage with two hydroxyl groups in a phosphate ion or a phosphate monoester is employed, and consequently have accomplished the invention.

A polyacrylamide gel for electrophoresis according to the invention is characterized in that at least a part of the structure thereof has a structure represented by the following formula (I); wherein $M^{2+}$ represents a transition metal ion; and X represents a linker group.

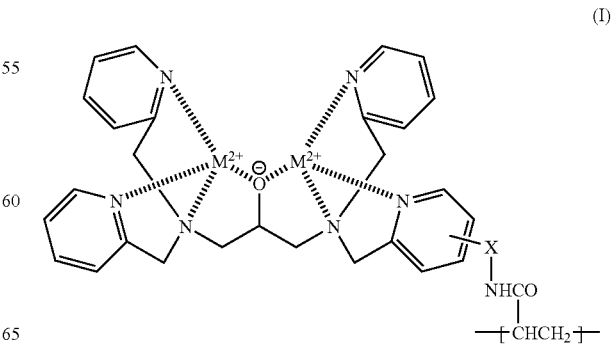

A polyacrylamide gel electrophoresis method of the invention employs the above-mentioned polyacrylamide gel for electrophoresis as a separation gel.

Further, a method of producing the polyacrylamide gel for electrophoresis according to the invention involves polymerizing an acrylamide mixed solution containing an acrylamide compound represented by the following formula (II) and/or transition metal complex thereof as a monomer, and the acrylamide compound (II) is important as a synthesizing intermediate compound to be used in the production method.

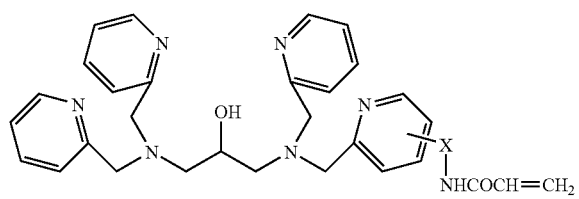

(II)

In the formula, X represents a linker group.

BRIEF DESCRIPTION OF THE DRAWINGS

FIG. 2 shows results of SDS-PAGE using the polyacrylamide gel for electrophoresis of the invention as a separation gel. FIGS. 2(1), (2), and (3) show results of α-casein, β-casein and ovalbumin, respectively, and the respective numerals of 0 to 150 show the concentration (μM) of the compound of the invention. The left side shows the results of phosphorylated type protein and the right side shows the results of dephosphorylated type protein in the respective columns. The polyacrylamide gel contains $Mn^{2+}$ as a transition metal ion.

DETAILED DESCRIPTION OF THE PREFERRED EMBODIMENTS

Figure 1:
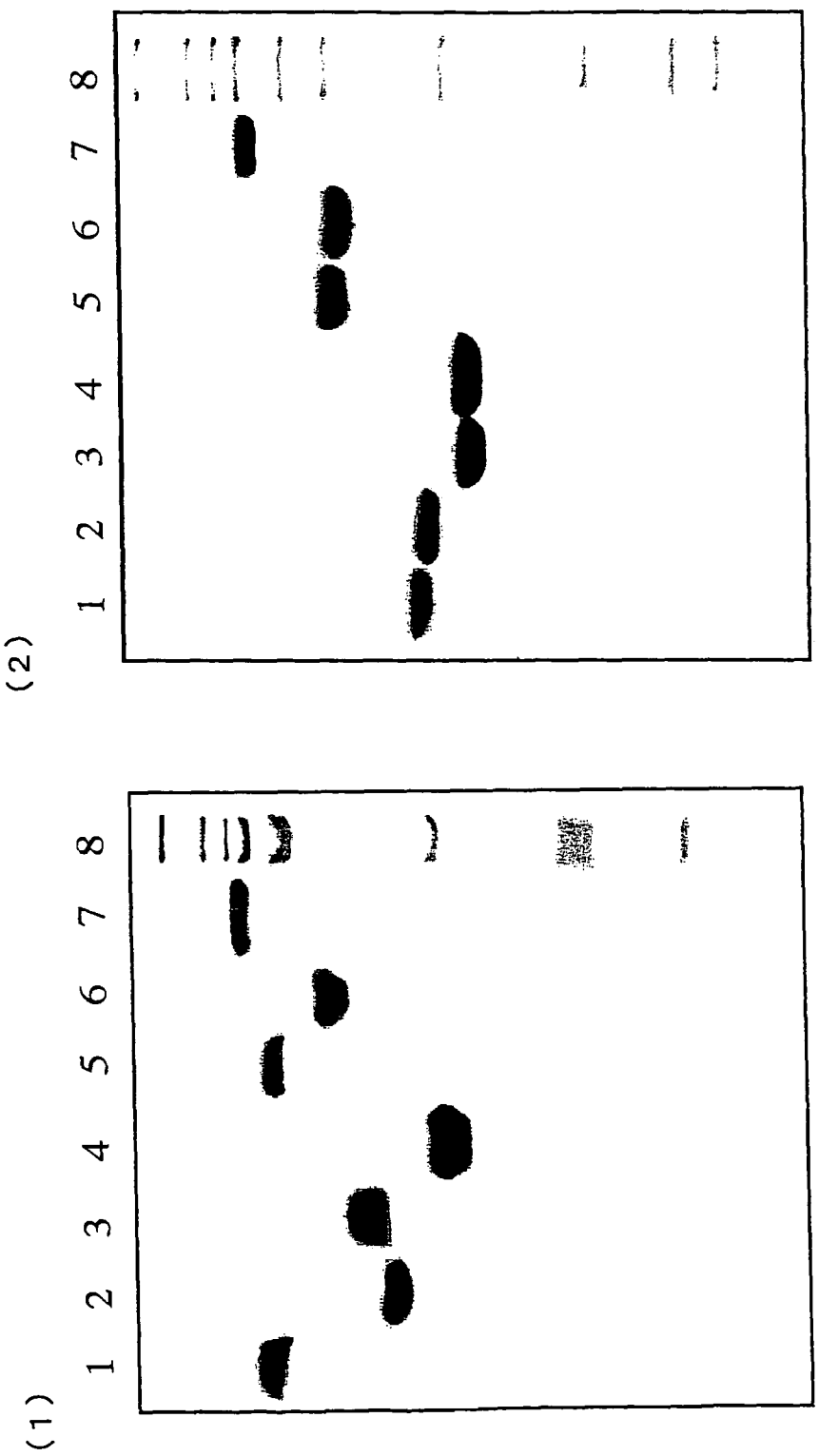
FIG. 1 shows results of SDS-PAGE using the polyacrylamide gel for electrophoresis of the invention (FIG. 1(1), separation gel A) and a conventional gel (FIG. 1(2), separation gel B) as a separation gel respectively. The polyacrylamide gel contains $Zn^{2+}$ as a transition metal ion.

Hereinafter, firstly, the method of producing polyacrylamide gel for electrophoresis of the invention will be described.

A separation gel to be used in SDS-PAGE (sodium dodecylsulfate-polyacrylamide gel electrophoresis) is produced generally by the following method: mixing an aqueous solution of an acrylamide mixture containing acrylamide and N,N'-methylenebisacrylamide, an aqueous solution containing SDS and ammonium persulfate, and a Tris (Tris(hydroxymethyl)aminomethane)-HCl buffer solution; further adding an aqueous solution of N,N,N',N'-tetramethylethylenediamine (TEMED); calmly mixing the mixture so as to entrain no foam; pouring the obtained mixture solution between glass plates; and still standing for polymerization. The key point of the polyacrylamide gel for electrophoresis of the invention is that the gel is characterized in that at least a part of the structure thereof has a structure represented by the following formula (I); wherein $M^{2+}$ represents a transition metal ion; and X represents a linker group.

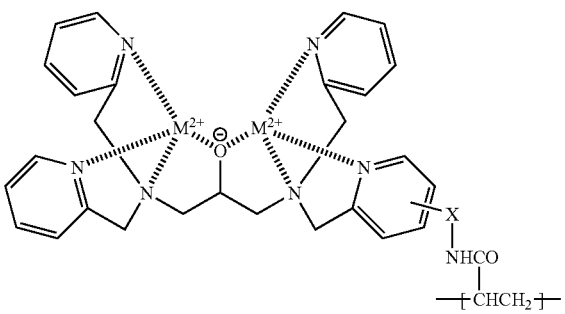

(I)

In the above-mentioned formula (I), the transition metal ion of $M^{2+}$ is preferably a divalent cation of a transition metal belonging to the fourth period. For example, $Mn^{2+}$, $Co^{2+}$, $Ni^{2+}$ and $Zn^{2+}$ may be properly selected and used. More specifically, $Mn^{2+}$ or $Zn^{2+}$ is preferable. In the acrylamide structure (I), a complex part, in which these transition metal ions are coordinated, has an extremely high coordination ability for a phosphoryl group (phosphate monoester group) of the phosphorylated protein.

The "linker group" is a group bonding the main part (hereinafter, sometimes referred to as "Phos-tag") having interaction property with phosphorylated peptide and an acrylamide part, and has a function of making the production of a precursor (monomer) of a polyacrylamide compound easy or making the coordination with the phosphorylated peptide easy by increasing the flexibility of the Phos-tag part.

Examples of the "linker group" are not particularly limited if they have the above-mentioned function, and may include a C1-C6 alkylene group, an amino group (—NH—), an ether group (—O—), a thioether group (—S—), a carbonyl group (—C(=O)—), a thionyl group (—C(=S)—), an ester group, an amido group, a urea group (—NHC(=O)NH—), a thiourea group (—NHC(=S)NH—), and a C1-C6 alkylene group having the group selected from a group consisting of an amino group, an ether group, a thioether group, a carbonyl group, a thionyl group, an ester group, an amido group, a urea group and a thiourea group at one terminal or both terminals.

Herein, a "C1-C6 alkylene group" means a straight or branched divalent aliphatic hydrocarbon group having 1 to 6 carbon atoms and may include, for example, methylene, ethylene, propylene, tetramethylene, hexamethylene, methylethylene, methylpropylene and dimethylpropylene and preferably a C1-C4 alkylene group and more preferably a C1-C2 alkylene group.

In the acrylamide structure (I), it is possible to introduce a common substituent such as methyl group into a pyridine ring as a substance having the same functional effect as that of the invention and such an equivalent substance is also within the scope of the invention.

Further, the substitution site of the linker group in the acrylamide structure (I) of the invention is not particularly limited and the linker group may exist at the site shown in the following structure (I').

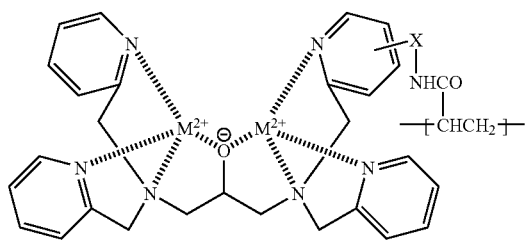

(I')

This structure (I') is completely equivalent to the structure (I). Although the site where a side chain exists is not necessarily clear, actually the structure is supposed to be a mixture of both and therefore, the structure (I') is also within the scope of the invention.

In the invention, it is essential that the structure (I) is in at least a part of the polyacrylamide gel, so at the time of producing the separation gel, an acrylamide compound represented by the following formula (II) and/or transition metal complex thereof as a monomer is added to the acrylamide mixed solution:

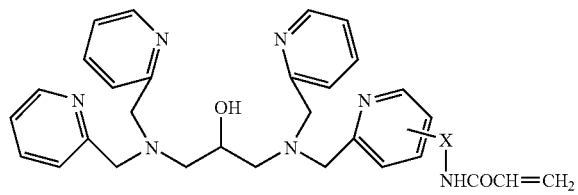

(II)

wherein X represents the above-mentioned linker group.

The acrylamide compound contained in the acrylamide mixed solution may be the acrylamide compound (II) entirely; however, it is preferable to add the compound (II) and/or transition metal complex thereof to the mixture of acrylamide and N,N'-methylenebisacrylamide which have been conventionally employed. It is because N,N'-methylenebisacrylamide has crosslinking function and also because it becomes difficult to form gel due to inhibition of polymerization by the bulky Phos-tag part in the case of using the compound (II) alone. On the other hand, as the ratio of the structure (I) is higher in the gel, the transfer distance of phosphorylated peptide becomes shorter and the separation and identification becomes easy correspondingly. The addition amount of the compound (II) is not particularly limited and may be arbitrarily selected to be optimum by preliminary experiments, in accordance with a test sample or the like. In general, the amount in mole ratio to acrylamide is preferably adjusted to be about $1 \times 10^{-7}$ to $1 \times 10^{-3}$, more preferably $1 \times 10^{-6}$ to $1 \times 10^{-4}$.

Further, since two transition metals or transition metal ions are coordinated in one Phos-tag part, a transition metal compound such as a transition metal salt is added in an amount at least two times as much as the molar equivalent to the compound (II). Addition of the transition metal compound is done at latest before the monomer is polymerized to form gel. It is because after the polymerization, coordination of the transition metal or transition metal ion becomes difficult. Although it is not clear that whether polymerization occurs after the coordination of the transition metal or transition metal ion with the compound (II) or whether the coordination of the transition metal or transition metal ion occurs after the polymerization, it is supposed that both occur probably simultaneously.

As the transition metal compound for coordinating the transition metal or transition metal ion, transition metal salts such as nitrates and acetates are preferably used. For example, in the case of coordination of $Zn^{2+}$, zinc nitrate or zinc acetate may be used and in the case of adding zinc acetate, it is supposed that a compound in which acetic acid is coordinated in the Phos-tag part as shown below is obtained.

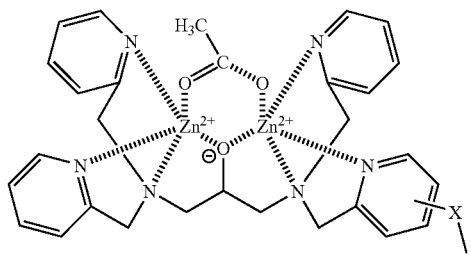

Although this structure is more stable than the structure (I), this structure is equivalent to the structure (I) and can be employed similarly to the structure (I). That is, at the time of electrophoresis, since the phosphate monoester group is coordinated reciprocally with acetic acid and interacted, phosphorylated peptide detection is made possible.

The polyacrylamide gel for electrophoresis of the invention is characterized in that at least a part of the structure thereof has a structure represented by the following formula (I) and it is supposed to be possible that a plurality of the structures (I) are adjacent to each another, however the structure (I) is highly possibly polymerized in a state adjacent to acrylamide or N,N'-methylenebisacrylamide. The structure of the gel may depend on the addition amount of the acrylamide compound (II) and the like, however, in the invention, the structure of the gel is not strictly limited as long as at least a part of the structure of the gel has the structure (I).

The acrylamide compound (II) of the invention can be easily produced by a method including the scheme 1, wherein X represents the above-mentioned linker group. However the production method is not limited to the following method.

Scheme 1

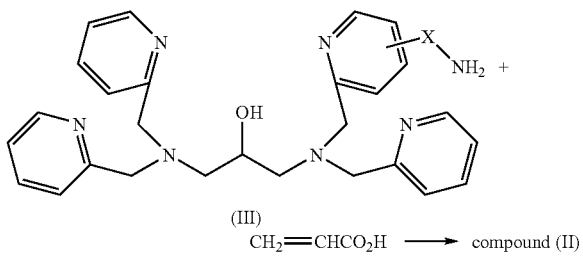

In the above-mentioned scheme 1, common amidation reaction of a carboxylic acid and an amine can be employed. For example, conventionally known methods such as the method in which a compound (III) and acrylic acid are reacted in the presence of a condensation agent such as a carbodiimide compound may be employed.

A solvent to be employed in the reaction of scheme 1 is not particularly limited if it properly dissolves the compound (III)

or the like therein and for example, halogenated hydrocarbons such as methylene chloride and chloroform may be used. Further, the condensation agent is also not particularly limited, and water-soluble carbodiimide is easy for post-treatment and therefore convenient.

The reaction may be carried out preferably at room temperature for about 30 minutes to 6 hours. After the completion of the reaction, distribution is carried out using, for example, water and a water-insoluble organic solvent. The obtained organic phase is concentrated and refined by a conventionally known method such as silica gel column chromatography.

In the above-mentioned scheme 1, the compound (III) can be produced by the following scheme 2.

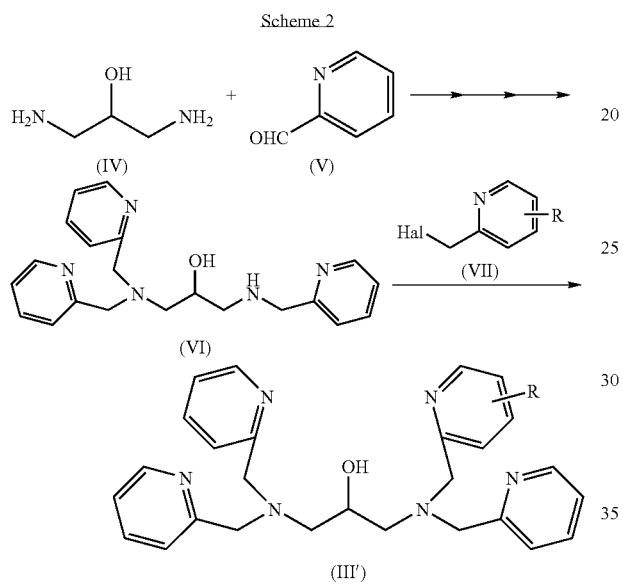

In the scheme 2, R represents a substituent easily convertible to —X—NH$_2$ or X—NH$_2$; "Hal" represents a halogen atom and preferably a bromine atom.

As a compound (IV) (1,3-diamino-2-propanol), which is a starting material compound, a commercialized compound can be employed. Since a compound (V) and a compound (VII) have relatively simple structures, commercialized compounds may be used or the compounds may be synthesized by a method known by a person skilled in the art.

In the scheme 2, at first, condensation reaction of the compounds (IV) and (V) is carried out in the presence of a catalyst to obtain the compound (VI). This reaction may be carried out by introducing the compound (V) step by step, or 3 or more equivalents of the compound (V) may be used to obtain the compound (VI) by one-step reaction.

In the scheme 2, reductive amination reaction is carried out as the condensation reaction. A solvent to be used in such a case is not particularly limited if it can substantially dissolve the compounds (IV) and (V) and does not inhibit the reaction, for example, usable solvents may be alcohols such as methanol, ethanol and isopropanol; ethers such as diethyl ether, tetrahydrofuran and dioxane; water; or their solvent mixtures.

In the reductive amination reaction, the compounds (IV) and (V) are firstly condensed in the presence of concentrated hydrochloric acid as a catalyst, and reduction is successively carried out using a common reducing reagent.

The reaction temperature and reaction time may be selected properly in accordance with the types of starting material compounds, however reaction may be carried out; for example, at 20 to 80° C. for 12 to 100 hours. After the completion of the reaction, the solvent or the like are removed in reduced pressure, water is added and then extraction is carried out using a nonaqueous solvent and after the oil phase is dried by magnesium sulfate anhydride or the like, the solvent is removed in reduced pressure. Successively, the residue is refined by a conventionally known method such as silica gel chromatography to obtain the compound (IV).

The method of obtaining the compound (VI) is not limited to the method shown in the scheme 2, and for example, synthesis may be carried out from the compound (IV) and a halogen compound.

Next, reaction with the compound (VII) is carried out to obtain a compound (III'). In this reaction, a common synthesis reaction of a tertiary amine may be employed. For example, condensation is carried out in the presence of a base in a solvent. Further, in this step, in accordance with the type of R, introduction of a protection group and de-protection may be properly carried out. Alternatively, in the place of R in the compound (VII), a compound having an inactive substituent is used to carry out the step and then the inactive substituent is converted into R$^2$ by converting the functional group to synthesize the compound (III'). For example, a compound having a nitro group as the inactive substituent is used and after the step, the nitro group may be converted into an amino group which is a reactive group. Further, for example, in the case where Phos-tag side terminal of the X group is an amido group or an ester group, reaction is carried out using the compound (VII) having a methyl ester group as the R group, and then ester interchange reaction is carried out to obtain the acrylamide compound (II).

The following structure may be used as the Phos-tag part to be used in the method of the invention:

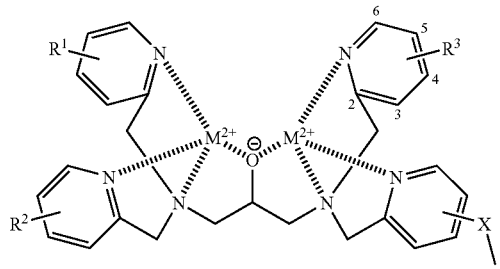

wherein M$^{2+}$ and X show the same meaning as those described above; R$^1$ to R$^3$ represent an electron donor type substituent at 4th or 6th site of the pyridine ring separately.

In the above-mentioned Phos-tag part, since the pyridine nitrogen becomes electron-rich due to the electron donor type substituent introduced into a proper substitution site, it is supposed that the pyridine nitrogen is excellent in coordination with M$^{2+}$ and as a result, the production is made easy and the Phos-tag part is stable.

Other steps of the electrophoresis method of the invention may be those in a conventional method. For example, common methods may be employed for condensed gel and electric current application and the like.

In conventional SDS-PAGE, since the electric charge of the peptides in a sample is canceled by SDS, the transfer distances of the respective peptides depend only on the molecular weights. Since the molecular weight of the peptide (protein) is rather much high as compared with those of common compounds, difference of the molecular weights so significant as to be detected by the electrophoresis cannot be caused only by phosphorylation. On the other hand, in the electrophoresis method of the invention, since the phosphorylated peptide in the sample is moved while interacting with the Phos-tag part in the separation gel, the transfer distance is apparently shortened. Accordingly, by comparison of the result of the electrophoresis method of the invention with the result of a conventional SDS-PAGE, it is made possible to easily specify the phosphorylated peptide.

The invention will be more specifically described with reference to the examples below, however the invention is not limited by the following examples. The application with appropriate modifications made in the scope matched with the true spirit of the invention is also possible, and the application with the modifications is also included in the technical scope of the invention.

EXAMPLES

Production Example 1-1

Methyl 6-Bromomethylnicotinate

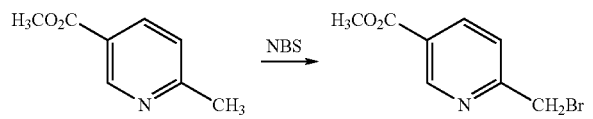

N-bromosuccinimide (59 g, 331 mmol) was added to a solution of methyl 6-methylniconitate (50 g, 331 mmol) in carbon tetrachloride (625 mL). Further, after benzoyl peroxide (1.0 g) was added, while light was radiated by a phototransmitter, reaction was carried out at 40 to 50° C. for 24 hours. After the reaction solution was cooled, the precipitated crystal was separated by filtration and the filtrate was washed with an aqueous sodium hydrogen carbonate solution and then concentrated. The obtained residue was refined by silica gel column chromatography to obtain 37 g of an aimed product.

$^1$H-NMR (CDCl$_3$, 300 MHz): δ3.96 (3H, s, OCH$_3$), 4.58 (2H, s, CH$_2$Br), 7.54 (1H, d, Py), 8.30 (1H, dd, Py), 9.17 (1H, d, Py)

Production Example 1-2

N,N,N'-tri(2-pyridylmethyl)-1,3-diaminopropan-2-ol

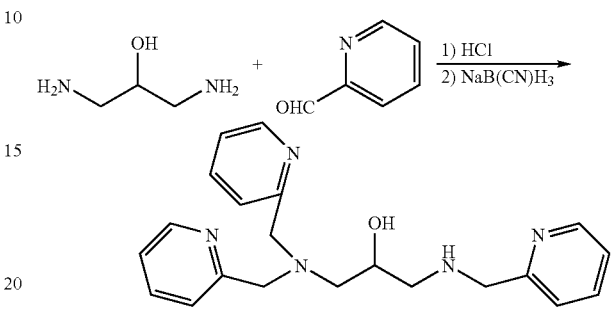

After concentrated hydrochloric acid (60 mL) was added to a solution of 1,3-diaminopropan-2-ol (32.6 g, 362 mmol) in methanol (2400 mL) and further 2-pyridine aldehyde (116.3 g, 1.09 mmol) was added dropwise, sodium cyanotrihydroborate (50.16 g, 798 mmol) was added. After the completion of the addition, reaction was carried out at room temperature for 3 days. After concentrated hydrochloric acid was added to the reaction solution to adjust pH to 6, the solution was concentrated to a proper extent and a 0.1 N aqueous sodium hydroxide solution was added to adjust pH to 7 and the solution was extracted using chloroform. The obtained chloroform phases were collected and dried and thereafter concentrated. The obtained residue was refined by silica gel column chromatography to obtain 34 g of an aimed product.

$^1$H-NMR (CDCl$_3$, 300 MHz): δ2.59-2.83 (4H, m, CH$_2$), 3.86-4.01 (7H, m, NCH$_2$Py, CH), 7.15 (3H, dd, Py), 7.23-7.32 (3H, m, Py), 7.56-7.65 (3H, m, Py), 8.53 (3H, dd, Py)

Production Example 1-3

N,N,N'-tri(2-pyridylmethyl)-N'-(5-methoxycarbonyl-2-pyridylmethyl)-1,3-diaminopropan-2-ol

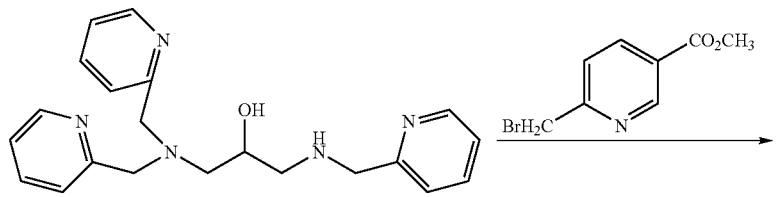

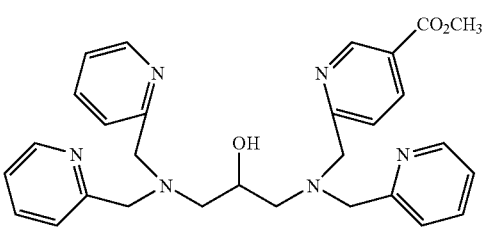

Potassium carbonate (13.8 g, 100 mmol) was added to a solution of N,N,N'-tri(2-pyridylmethyl)-1,3-diaminopropan-2-ol (18.2 g, 50 mmol) obtained in Production example 1-2 in absolute dimethylformamide (150 mL) and a solution of methyl 6-bromomethylnicotinate (11.5 g, 50 mmol) obtained in Production example 1-1 in absolute dimethylformamide (75 mL) was added dropwise. After completion of the addition, reaction was carried out at 50° C. for 1 hour. After the reaction, the solution was cooled and thereafter poured to 750 mL of water to adjust pH to 8 by 1N hydrochloric acid. After extraction with ethyl acetate, the obtained ethyl acetate phases were collected, washed with water and saturated saline, and successively concentrated. The obtained residue was refined by silica gel column chromatography to obtain 21.5 g of an aimed product.

$^1$H-NMR (CDCl$_3$, 300 MHz): δ2.58-2.73 (4H, m, CH$_2$), 3.83-3.95 (12H, m, OCH$_3$, NCH$_2$Py, CH), 7.10-7.14 (3H, m, Py), 7.34 (3H, d, Py), 7.50-4.60 (4H, m, Py), 8.17 (1H, dd, Py), 8.50 (3H, d, Py), 9.09 (1H, d, Py)

Production Example 1-4

N,N,N'-tri(2-pyridylmethyl)-N'-[5-N"-(2-aminoethyl)carbamoyl-2-pyridylmethyl]-1,3-diaminopropan-2-ol

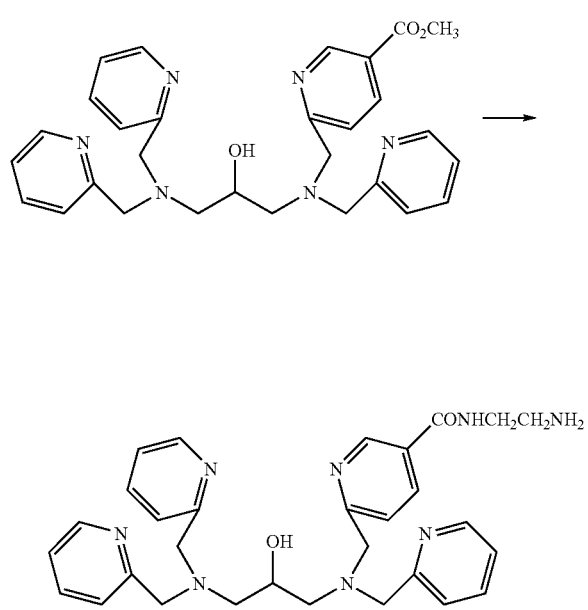

Ethylenediamine (22.7 g, 378 mmol) was dropwise added to a solution of N,N,N'-tri(2-pyridylmethyl)-N'(5-methoxycarbonyl-2-pyridyl methyl)-1,3-diaminopropan-2-ol (9.7 g, 18.9 mmol) obtained in Production example 1-3 in methanol (100 mL). After completion of the addition, reaction was carried out at room temperature for 3 days. After the reaction, the solution was concentrated and the obtained residue was refined by silica gel column chromatography to obtain 9.72 g of an aimed product.

$^1$H-NMR (CDCl$_3$, 300 MHz): δ2.54-2.71 (4H, m, CH$_2$), 2.94 (2H, t, CH$_2$N), 3.49 (2H, dt, CH$_2$N), 3.80-3.99 (9H, m, NCH$_2$Py, CH), 7.12 (3H, ddd, Py), 7.35 (3H, d, Py), 7.45 (1H, d, Py), 7.58 (3H, ddd, Py), 8.02 (1H, dd, Py), 8.49 (3H, ddd, Py), 8.89 (1H, d, Py)

Production Example 1-5

Acrylamide Compound

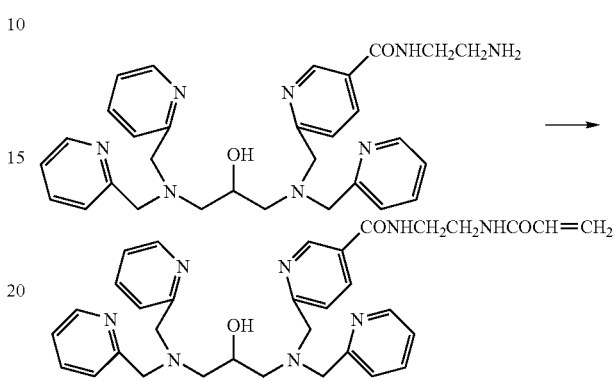

Acrylic acid (35.3 mg, 49 mmol) was added to a solution containing N,N,N'-tri(2-pyridylmethyl)-N'-[5-N"-(2-aminoethyl)carbamoyl-2-pyridylmethyl]-1,3-diaminopropan-2-ol (220 mg, 0.37 mmol) obtained in Production example 1-4 and hydroquinone monomethyl ether (0.35 mg) in methylene chloride (20 mL) and successively 1-ethyl-3-(3-dimethylaminopropyl) carbodiimide hydrochloride (93.5 mg, 49 mmol) was added to carry out reaction at room temperature for 75 minutes. After the completion of the reaction, water was added to the reaction solution and the water phase was extracted with chloroform. A crude product obtained by collecting and concentrating the organic phases was refined by column chromatography to obtain 237 mg of an aimed product (98% yield).

$^1$H-NMR (CDCl$_3$, 300 MHz): δ2.60-2.66 (4H, m, CH$_2$), 3.62 (4H, bs, NCH$_2$CH$_2$N), 3.78-3.91 (9H, m, NCH$_2$Py, CH), 5.65 (1H, dd, CH=CH$_2$), 6.11 (1H, dd, CH=CH$_2$), 6.30 (1H, dd, CH=CH$_2$), 6.72 (1H, bs, NHCO), 7.12 (3H, ddd, Py), 7.35 (3H, dd, Py), 7.45 (1H, d, Py), 7.58 (3H, ddd, Py), 7.82 (1H, bs, NHCO), 8.00 (1H, dd, Py), 8.49 (3H, dd, Py), 8.90 (1H, d, Py)

Production Example 1-6

Production of Gel for Electrophoresis

Using the acrylamide compound obtained in the above Production example 1-5, each separation gel with the composition as shown in Table 1 was produced. Each concentration gel with the composition as shown in Table 1 was also produced. The solvent for the respective solutions was distilled water or re-distilled water.

TABLE 1

| | Separation gel | Concentration gel |
|---|---|---|
| Acrylamide compound of Production example 1-5 | 0.10 mM | — |
| Zn (CH$_3$COO)$_2$ | 0.20 mM | — |
| Acrylamide mixture*[1] | 12.5% (w/v) | 4.5% (w/v) |
| Tris-HCl (pH 6.8) | 125 mM | 375 mM |
| SDS | 0.1% (w/v) | 0.1% (w/v) |

TABLE 1-continued

|  | Separation gel | Concentration gel |
|---|---|---|
| Ammonium peroxide | 0.48% (w/v) | 0.17% (w/v) |
| TEMED*[2] | 0.71% (v/v) | 2.5% (v/v) |

*[1] acrylamide:N,N'-methylenebisacrylamide = 29:1
*[2] N,N,N',N'-tetramethylethylenediamine Reagents other than TEMED of each separation gel composition shown in Table 1 were charged in a 50 mL-plastic centrifugation tube and moderately mixed at room temperature until the obtained solution became homogenous. At that time, the mixture was mixed sufficiently carefully to prevent foam formation. Next, while the end of the tip of a micro-pipette was immersed in separation gel solution, TEMED was added and mixed immediately at room temperature. In this case, the mixture was mixed carefully to prevent foam formation.

Separately, a gel production kit (AE-6401 model mini-slab gel production kit) manufactured by ATTO Corporation was used to assemble mini-slab gel plate (inner thickness: 1 mm, inner width: 90 mm). Each separation gel described above was poured in the gel plate up to a height of 70 mm without forming foams. At that time, the gel plate was stood upright on a lab bench and it was confirmed that the top face of the separation gel was horizontal.

Next, distilled water was calmly overlaid on the top face of the separation gel by using a micro-pipette. The amount of the distilled water to be overlaid was approximated to be at about 1 cm height from the top face of the separation gel. While being kept still at room temperature for 1 hour, the separation gel was hardened. Hereinafter, the separation gel is referred to as "separation gel A". After the hardening of the separation gel was confirmed and the overlaid distilled water was removed, concentration gel was prepared.

Each concentration gel solution with the composition shown in Table 1 was prepared by the same method as that of the separation gel solution preparation and poured on the above-mentioned separation gel. Next, a mini-comb was inserted to form wells for filling samples and the concentration gel solution was kept at room temperature for 1 hour to harden the concentration gel.

After the hardening of the concentration gel was confirmed, the mini-comb was slowly pulled out. The wells for filling samples formed accordingly were filled with an electrophoresis buffer having the composition shown in Table 2 by a micro-pipette. After the electrophoresis buffer was removed, the same treatment was carried out again to wash the wells. After the washing of the wells, a seal gasket was disassembled from the mini-slab gel plate to complete a gel plate.

TABLE 2

| Electrophoresis buffer | |
|---|---|
| Tris-0.19M glycine (pH 6.8) | 125 mM |
| SDS | 0.1% (w/v) |

Further, as a comparative reference, a separation gel with the same composition in Table 1 except that the acrylamide compound of Production example 1-5 and zinc acetate were not added was prepared. Hereinafter, the separation gel containing no Phos-tag is referred to as "separation gel B".

Test Example 1

A buffer with the composition shown in Table 3 for sample preparation was prepared.

TABLE 3

| Buffer for sample preparation | |
|---|---|
| Tris - HCl (pH 6.8) | 65 mM |
| SDS | 3.0% (w/v) |
| Glycerol | 10% (v/v) |
| 2-mercaptoethanol | 5.0% (v/v) |
| Bromophenol blue | 0.033% (w/v) |

Separately, $\alpha S_1$-casein (M.W. 24,000), (β-casein (M.W. 25,000) and ovalbumin (M.W. 45,000) (all manufactured by Sigma-Aldrich Co.), which are phosphorylated proteins, were dephosphorylated by being treated at 37° C. for 12 hours by 3.3 units of alkali phosphatase in 50 mM Tris-HCl (pH 9.0)+10 mM $MgCl_2$. Among the respective proteins shown in Table 4, the sample Nos. 1, 3, and 5 were dissolved in 1 μL of the buffer for sample preparation; sample Nos. 2, 4, 6 and 7 were dissolved in 3 μL of the buffer to obtain the respective samples. The bovine serum albumin was manufactured by Takara Shuzo Co., Ltd. and the molecular weight was 66,000, and the molecular weight markers were Protein molecular weight standards manufactured by Amersham Bioscience.

TABLE 4

| Sample No. | Protein | | |
|---|---|---|---|
| 1 | $\alpha S_1$-casein | Phosphorylated type | 3 μg |
| 2 | $\alpha S_1$-casein | Dephosphorylated type | 3 μg |
| 3 | β-casein | Phosphorylated type | 3 μg |
| 4 | β-casein | Dephosphorylated type | 3 μg |
| 5 | Ovalbumin | Phosphorylated type | 3 μg |
| 6 | Ovalbumin | Dephosphorylated type | 3 μg |
| 7 | Bovine serum albumin | — | 3 μg |
| 8 | Molecular weight marker | — | 2 μL |

The gel plate produced in the above-mentioned Production example 1-5 was set in AE-6500 type Rapidus Mini-slab electrophoresis apparatus manufactured by ATTO Corporation, and the respective protein samples were charged in the wells. However, the molecular markers were charged directly without being mixed with the buffer for sample preparation. Electrophoresis was carried out at 20 mA for 90 minutes for the separation gel A containing Phos-tag and at 40 mA for 45 minutes for the conventional separation gel B using iMyRun type power supply manufactured by Cosmo Bio Co., Ltd.

After electrophoresis, the gel was disassembled and dyed by immersing the gel in a dye solution (3.0 mM Coomassie Brilliant Blue R-250+45% (v/v) methanol+1.2% (v/v) acetic acid) at room temperature overnight. Next, the gel was decolorized by immersing the gel in a decolorization solution (25% (v/v) methanol+10% (v/v) acetic acid) at room temperature for 5 hours. The photograph of the obtained gel is shown as FIG. 1.

According to the results, in the case of using the conventional gel (separation gel B), with respect to the same proteins, the bands of phosphorylated and dephosphorylated proteins are at the same positions. On the other hand, in the case of carrying out electrophoresis using the gel of the invention (separation gel A), the band transfer distance of the phosphorylated proteins (sample Nos. 1, 3, and 5) is apparently short as compared with that of the dephosphorylated one of the same proteins (sample Nos. 2, 4, and 6). Accordingly, it is proved that if the gel for electrophoresis of the invention is employed, a phosphorylated or dephosphorylated protein can be easily specified.

Production Example 2

Production of Gel for Electrophoresis

Separation gel was produced in the same manner as in the above-mentioned Production example 1-6 using the acrylamide compound obtained in the above-mentioned Production example 1-5, except that the composition was changed to the composition shown in Table 5. The addition amount of $MnCl_2$ was 2 equivalents to that of the acrylamide compound.

TABLE 5

|  | Separation gel | Concentration gel |
| --- | --- | --- |
| Acrylamide compound of Production example 1-5 | 0, 50, 100 or 150 µM | — |
| $MnCl_2$ | 0, 100, 200 or 300 µM | — |
| Acrylamide mixture*[1] | 10% or 7.5% (w/v) | 4.5% (w/v) |
| Tris - HCl (pH 8.8) | 375 mM | — |
| Tris - HCl (pH 6.8) | — | 125 mM |
| Sodium dodecylsulfate | 0.1% (w/v) | 0.1% (w/v) |

*[1] acrylamide:N,N'-methylenebisacrylamide = 29:1

Further, an electrophoresis buffer having the composition shown in Table 6 was separately prepared and a gel plate was produced in the same manner as that in the Production example 1-6 using the electrophoresis buffer.

TABLE 6

| Electrophoresis buffer | |
| --- | --- |
| Tris | 25 mM |
| Glycine | 192 mM |
| Sodium dodecylsulfate | 0.1% (w/v) |

Test Example 2

A buffer with the composition shown in Table 7 for sample preparation was prepared.

TABLE 7

| Buffer for sample preparation | |
| --- | --- |
| Tris - HCl (pH 6.8) | 195 mM |
| Sodium dodecylsulfate | 9% (w/v) |
| Glycerol | 24% (v/v) |
| 2-mercaptoethanol | 15% (v/v) |
| Bromophenol blue | 0.1% (w/v) |

Samples were obtained by mixing 1.0 µL of each aqueous solution of the proteins (0.3 µg/L) shown in Table 8 and 6.0 µL of distilled water to 3.0 µL of the buffer for sample preparation. The molecular weight markers were Protein molecular weight standards manufactured by Amersham Bioscience.

TABLE 8

| Sample No. | Protein | |
| --- | --- | --- |
| 9 | $\alpha s_1$-casein | Phosphorylated type |
| 10 | $\alpha s_1$-casein | Dephosphorylated type |
| 11 | β-casein | Phosphorylated type |
| 12 | β-casein | Dephosphorylated type |
| 13 | Ovalbumin | Phosphorylated type |
| 14 | Ovalbumin | Dephosphorylated type |

Using the gel plate produced in Production example 2, electrophoresis was carried out for the above-mentioned sample Nos. 9 to 14 in the same conditions described in the above-mentioned Test example 1 and thereafter, the gel plate was dyed. The photograph of the obtained gel is shown as FIG. 2. In FIG. 2, results of (1) α-casein, (2) β-casein and (3) ovalbumin are shown respectively, the numerals of 0 to 150 represent the concentration (µM) of the compound of the invention, and the left side shows the results of phosphorylated type proteins and the right side shows the results of dephosphorylated type proteins in the respective columns.

As shown in the results, Rf value becomes smaller as the concentration of the acrylamide compound of the invention in the gel is increased, even in the case of electrophoresis of the dephosphorylated proteins. However, the Rf values for the phosphorylated proteins are apparently smaller than the Rf values of the dephosphorylated proteins. According to the results, it is proved that when the gel for electrophoresis of the invention is used, not only in the case of using $Zn^{2+}$ but also in the case of using $Mn^{2+}$ as a transition metal ion, a phosphorylated or dephosphorylated protein can be easily specified.

INDUSTRIAL APPLICABILITY

If SDS-PAGE is carried out using the polyacrylamide gel for electrophoresis of the invention, as compared with the case of using a common gel, the transfer distance of the band of a phosphorylated peptide (protein) is apparently shortened. Accordingly, from the fact that even in a test sample containing various kinds of compounds such as a biological sample, existence of the phosphorylated peptide (protein) can be easily determined, the polyacrylamide gel for electrophoresis of the invention and the electrophoresis method of the invention are remarkably advantageous in aspects of applicability to diagnosis of disease and the like.

The production method and the synthesizing intermediate in producing the gel, an acrylamide compound, of the invention are useful to be employed for producing such a polyacrylamide gel for electrophoresis.

The invention claimed is:

1. A polyacrylamide gel for electrophoresis characterized in that at least a part of the structure thereof has a structure represented by the following formula (I):

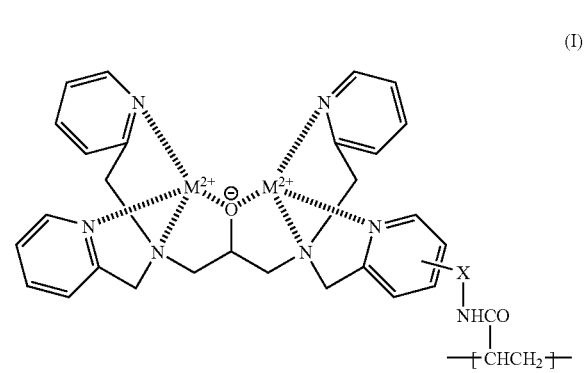

(I)

wherein $M^{2+}$ represents a transition metal ion; and X represents a linker group.

2. The polyacrylamide gel for electrophoresis according to claim 1, wherein $M^{2+}$ represents a divalent cation of a transition metal belonging to the fourth period.

3. The polyacrylamide gel for electrophoresis according to claim 1, wherein $M^{2+}$ represents $Mn^{2+}$ or $Zn^{2+}$.

4. A polyacrylamide gel electrophoresis method, comprising the steps of:
carrying out sodium dodecylsulfate-polyacrylamide gel electrophoresis (SDS-PAGE) using the polyacrylamide gel for electrophoresis according to claim 1 as a separation gel; separately carrying out SDS-PAGE using a conventional polyacrylamide gel for electrophoresis as a separation gel; and
comparing the results of the SDS-PAGE to specify a phosphorylated peptide.

5. A method of producing a polyacrylamide gel for electrophoresis comprising polymerizing an acrylamide mixed solution containing an acrylamide compound represented by the following formula (II) and/or a transition metal complex thereof as a monomer:

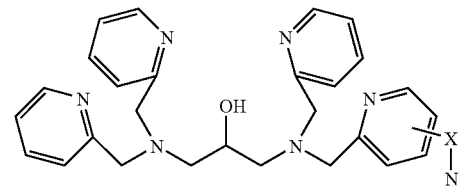

(II)

wherein X represents a linker group.

6. An acrylamide compound represented by the following formula (II):

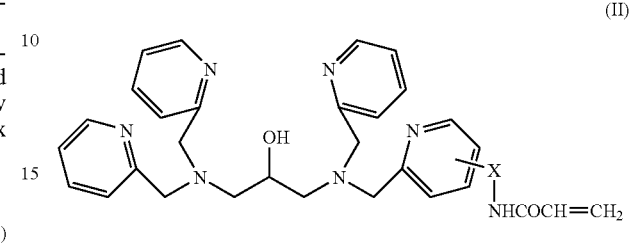

(II)

wherein X represents a linker group.

* * * * *